(12) United States Patent
Ghassemi et al.

(10) Patent No.: US 11,903,740 B2
(45) Date of Patent: Feb. 20, 2024

(54) METHOD AND DEVICE FOR THE PASSIVE RECORDING OF THE ELECTROCARDIOGRAM WHILE WORKING AT A DESK

(71) Applicants: Mohammad Mahdi Ghassemi, Cambridge, MA (US); Julian Euma Ishii-Rousseau, Davis, CA (US)

(72) Inventors: Mohammad Mahdi Ghassemi, Cambridge, MA (US); Julian Euma Ishii-Rousseau, Davis, CA (US)

( * ) Notice: Subject to any disclaimer, the term of this patent is extended or adjusted under 35 U.S.C. 154(b) by 241 days.

(21) Appl. No.: 16/183,713

(22) Filed: Nov. 7, 2018

(65) Prior Publication Data
US 2021/0128064 A1 May 6, 2021

(51) Int. Cl.
| | | |
|---|---|---|
| A61B 5/24 | (2021.01) | |
| A61B 5/28 | (2021.01) | |
| A61B 5/00 | (2006.01) | |
| A61B 5/282 | (2021.01) | |
| A61B 5/336 | (2021.01) | |
| A61B 5/308 | (2021.01) | |
| A61B 5/346 | (2021.01) | |

(52) U.S. Cl.
CPC ............ *A61B 5/6887* (2013.01); *A61B 5/002* (2013.01); *A61B 5/0006* (2013.01); *A61B 5/282* (2021.01); *A61B 5/308* (2021.01); *A61B 5/336* (2021.01); *A61B 5/346* (2021.01); *A61B 5/6843* (2013.01); *A61B 5/6891* (2013.01); *A61B 5/6892* (2013.01); *A61B 5/6897* (2013.01); *A61B 2503/24* (2013.01); *A61B 2560/0468* (2013.01); *A61B 2562/0209* (2013.01)

(58) Field of Classification Search
CPC ....... A61B 5/6891; A61B 5/346; A61B 5/282; A61B 5/308; A61B 5/301; A61B 5/336; A61B 5/0006; A61B 5/002; A61B 5/6843; A61B 5/6892; A61B 5/6897; A61B 2503/24; A61B 2560/0468; A61B 2562/0209
See application file for complete search history.

(56) References Cited

U.S. PATENT DOCUMENTS

| | | | | |
|---|---|---|---|---|
| 2006/0041201 A1* | 2/2006 | Behbehani | ........... | A61B 5/4818 |
| | | | | 600/521 |
| 2006/0264767 A1* | 11/2006 | Shennib | ................... | A61B 5/25 |
| | | | | 600/509 |

(Continued)

FOREIGN PATENT DOCUMENTS

CN 101605495 B * 4/2014 ............... A61B 5/00

OTHER PUBLICATIONS

Flore Ingo, Kyung Cho Ok, Ok Kim Yoon, CN 101605495 Translation "Medical Measuring Device", Dec. 16, 2009 (Year: 2009).*

*Primary Examiner* — Adam Z Minchella
(74) *Attorney, Agent, or Firm* — MYERS WOLIN, LLC

(57) ABSTRACT

The invention comprises a system that monitors heart activity through embedded ECG sensors in a desk, and desk-related amenities such as a chair, a computer keyboard, a mouse, and a floor mat. The invention also comprises pressure sensors for monitoring a user's presence at the desk. Signals measured from the ECG or pressure sensors are transmitted (in a wired, or wireless fashion) to a computer processing device which applies algorithms to refine the collected signals, and passively estimate the user's ECG.

3 Claims, 7 Drawing Sheets

(56) References Cited

U.S. PATENT DOCUMENTS

| | | | |
|---|---|---|---|
| 2014/0046144 A1* | 2/2014 | Jayaraman | A61B 5/1116 |
| | | | 600/509 |
| 2014/0163333 A1* | 6/2014 | Horseman | A61B 5/6897 |
| | | | 600/301 |
| 2016/0157781 A1* | 6/2016 | Baxi | A61B 5/302 |
| | | | 600/372 |
| 2017/0202464 A1* | 7/2017 | Tsao | A61B 5/282 |
| 2018/0197425 A1* | 7/2018 | Lamb | A61B 5/6891 |
| 2019/0142294 A1* | 5/2019 | Govari | A61B 5/6801 |
| | | | 257/307 |

* cited by examiner

METHOD AND DEVICE FOR THE PASSIVE RECORDING OF THE ELECTROCARDIOGRAM WHILE WORKING AT A DESK

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not applicable

INCORPORATION-BY-REFERENCE OF MATERIAL SUBMITTED ON A COMPACT DISC

Not applicable

STATEMENT REGARDING PRIOR DISCLOSURES BY INVENTORS

Not applicable

FIELD

The invention relates to a passive data collection system that monitors an individual's heart while seated at a desk. The device uses electrocardiographic (ECG) physiological sensors, embedded into a desk or within desk-related amenities to capture heart activity; the invention also comprises pressure sensors for monitoring a user's presence at the desk. The invention transmits these activities to a remote computer device for further storage, processing, and analysis.

BACKGROUND OF THE INVENTION

At present, cardiovascular diseases (CVD) are the leading cause of death worldwide and by 2030 the total global cost is projected to be at 1.044 trillion dollars. Actionable insights that result from passive health data collection strategies may alleviate CVD global burden as well as mortality rates.

Since Dr. Carlo Matteucci demonstrated that an electric current accompanies each heartbeat in 1828, humans have searched for methods to better collect and understand the relationship between the heart and electricity. In 1887, Dr. Augustus Waller published the first human ECG using a capillary electrometer, and in 1902, Dr. Willem Einthoven improved the measurements using a string galvanometer to record the ECG; he was awarded the Nobel Prize for his work in 1924.

Einthovens ECG used three bipolar leads located at the right arm, left arm, and left leg. The ECG generated a novel graphical representation of the direction and magnitude of the heart's electrical field with respect to time. Since the early 1900s, ECG devices have evolved to become the 12-lead device used today; in addition to the original three bipolar leads, the current standard 12-lead device records signals from three augmented limb leads (hex-axial reference system) and six precordial leads (Wilson central terminal) placed on a patients chest or limbs.

Patients at high risk of, or currently diagnosed with, CVD would receive portable monitors for recording a continuous ECG. Recent portable models include AliveCor's Kardia-Mobile and HeartCheck's PEN handheld ECG device. Both products are lightweight, efficient, and affordable, permitting instant ECG analysis and data sharing with doctors. The challenge of portable monitors is that they require an active effort on the part of the users to record their ECG; users must interrupt their daily activities to take a measurement.

The challenges of portable ECG monitors are partially addressed by existing wearable devices (e.g. Apple watch or Fitbit) which can capture real-time ECG data, and are already used to monitor patients with chronic disease. For instance, the Apple Watch (series 4) allows users to measure their ECG by placing a finger on the crown of the watch. However, there are limitations to the passive collection of health data through wearable devices. The energy densities of existing battery technologies do not allow for devices that are both low-weight/volume and sustain a long battery life; this limits the potential of wearable devices for consistent passive monitoring. Furthermore, even the latest wearable devices still require users to actively opt-in for high-value data collection (e.g. Apple Watch (series 4) requires users to put their finger on the digital crown to measure their ECG).

Passive health monitoring systems permit automated health data collection without interrupting daily life. Passive monitoring has proven to be effective in decreasing medical costs and to have a positive impact on healthcare provider efficiency. However, passive health monitoring technology requires ubiquitous and automatic sensors to obtain data without intrusion. The creation of a truly passive heart monitoring method, permitting daily surveillance and data collection is essential for further understanding and prevention of CVD. Herein we present an invention for the passive monitoring of the ECG that does not require a wearable device, or opt-in for data collection. The invention monitors an individual's heart while seated at a desk using ECG physiological sensors, embedded into a desk or within desk-related amenities; it transmits this activity to a remote computer device for further storage, processing, and analysis. The invention will allow for passive heart monitoring, without the constraints of existing wearable devices.

RELATED PRIOR DISCLOSURES

The related prior art is of three varieties: (1) portable ECG devices, (2) ECG embedded within seating devices and (3) desks systems for general-purpose health monitoring; We describe these domains of related prior art below.

The oldest patent concerning the ECG (GB802717A) was filed by the National Research Council on Jan. 21, 1957. The patent describes an electronic apparatus with an additional amplifier that automatically shifts gating circuits for improved observation of heart sounds. Examples of portable ECG monitors include (U.S. Pat. No. 5,191,891A), a wrist-worn apparatus that selectively monitors, records, and transmits ECG data, (U.S. Pat. No. 6,871,089B2) a portable ECG monitor that detects atrial fibrillation, and (US20120191147A1) a skin patch sensor device for real-time medical data collection and (KR101649445B1) a "non-contact" ECG sensor device that can be integrated into objects. Excepting (KR101649445B1), the aforementioned inventions require users to actively opt-in to ECG measurements by placing their skin on the sensors.

(US20150297433A1A) describes a table on which patients lie, that supports various cable channels and equipment ranging from ECG, SPO2, to blood pressure cuffs and transducers.

The prior art also describes multiple chair-based devices that collect the ECG. (KR20130137327A) collects the ECG data through a system integrated into various parts of the chair (seat, back, etc.). (DE4217388A1) integrates the ECG leads within a blood pressure cuff that resides on the arm chair. Similarly, (FR3041876A1) describes a chair that measures the ECG data from the arm rests and foot rests of a chair. (US20110034784A1) is an expansion of (FR3041876A1)'s concept by incorporating other types of physiological sensors (e.g. finger-tip sensors etc.), in addition to a device that processes and transmits data. Importantly, the four inventions above do not extend beyond the chair; they also do not incorporate software to capture a refined measure of heart activity (excepting KR101649445B1).

Related prior research includes portable ECG devices, wireless sensors, non-contact sensors, and noise reduction methods. Wei et al. described a portable ECG (https://ieeexplore.ieee.org/abstract/document/4535543) device with a bluetooth module to collect and analyze ECG data on a computer. Nemati et al. (https://ieeexplore.ieee.org/document/6122530), proposed a wearable ECG sensor that permits low-rate wireless ECG data transmission under the ANT protocol. Lim et al. (https://ieeexplore.ieee.org/document/1621147), described a non-contact ECG sensor technology embedded in chairs permitting data collection through clothes. Wu et al. (https://ieeexplore.ieee.org/abstract/document/4201276), describe a non-contact blood pressure monitoring system using e-textile materials. Finally, Lee et al. (http://citeseerx.ist.psu.edu/viewdoc/download?doi=10.1.1.639.9471rep=repltype=pdf), proposed a non-contact ECG measurement system using CC-electrodes and an electrical circuit to reduce noise.

The closest related prior art is (U.S. Pat. No. 9,949,640B2), a combination of a chair, desk, and mat measuring body position, temperature, and body fat composition. The work station is structurally similar to the invention described herein, with the following important distinctions: (1) the prior art measures heart-rate, the proposed invention measures ECG, (2) the prior art captures heart activity using a single sensor, the proposed invention uses a set of distributed sensors, (3) the prior art only captures raw heart activity, the proposed invention applies algorithms to the capture a refined measurement of heart activity.

Notably, none of the related prior disclosures collect data using sensors distributed across multiple devices (on a desk, chair, keyboard, mouse or mat) as seen with the invention herein. Furthermore, the related prior disclosures do not apply algorithms for noise reduction as seen with the invention herein.

BRIEF SUMMARY OF THE INVENTION

The disclosed invention describes a device that passively measures and analyzes the heart's electrical activity. The device measures the heart's electrical activity using a set of electrically conductive metal sheets; these metal sheets are embedded within a set of work-related objects: desk, chair, computer keyboard, computer mouse, and floor mat. A subset of the embedded metal sheets make contact with an individual's skin as they use the work-related objects (or items upon it). Signals measured from the embedded electrically conductive metal sheets are transmitted (in a wired, or wireless fashion) to a receiver attached to one or more of the work-related objects. The receiver stores the collected signal data on a computer processing device. The computer processing device applies algorithms to refine the collected signals, and estimate the user's ECG.

BRIEF DESCRIPTION OF THE SEVERAL VIEWS OF THE DRAWINGS

The embodiment of the present invention is illustrated by way of example in, and not limited to, the following figures.

DETAILED DESCRIPTION OF THE INVENTION

The best mode for carrying out the invention follows. A specific embodiment of the invention will be described with reference to the accompanying figures. The method of passively collecting the ECG is applicable to various furniture or objects and is not limited to the particular configuration outlined herein. Furthermore, the particular configuration outlined herein may be used to collect other health signals beyond the ECG (e.g. Galvanic skin response, respiratory rate, temperature). Therefore, the invention herein is not limited to a single form and the following descriptions and figures are not intended to limit the invention to a single form, instantiation, or implementation.

In brief, we propose a device that measures the heart's electrical activity using a set of electrically conductive materials; these materials are embedded within a set of work-related objects: an office desk, an office chair, a computer keyboard, a computer mouse, and a floor mat. Within the office chair, electrically conductive metal sheets are located in the left and right arm of the chair. Within the computer mouse is an electrically conductive metal sheet integrated into the palm-rest. Each key on the computer keyboard contains electrically conductive metal cylinder. Within the floor mat are two electrically conductive areas situated such that a user's left foot and right foot would make contact while seated at the desk. A subset of the embedded electrically conductive metal materials make contact with an individual's skin as they use the work-related objects (or items upon it). Signals measured from the embedded electrically conductive materials are transmitted to a receiver. The receiver stores the collected signal data on a computer processing device. The computer processing device applies an algorithm to refine the collected signals, and estimate the user's ECG. The algorithm proceeds through a sequence of steps that refine the collected signals; these steps include: (1) 1-40 Hz band-pass filter, (2) burst noise detection, (3) burst noise removal, (4) independent component analysis, and (5) independent component selection. Note, the seat and lumbar support of the chair also contain force-sensitive resistors that detects a user's presence.

Figure 1:
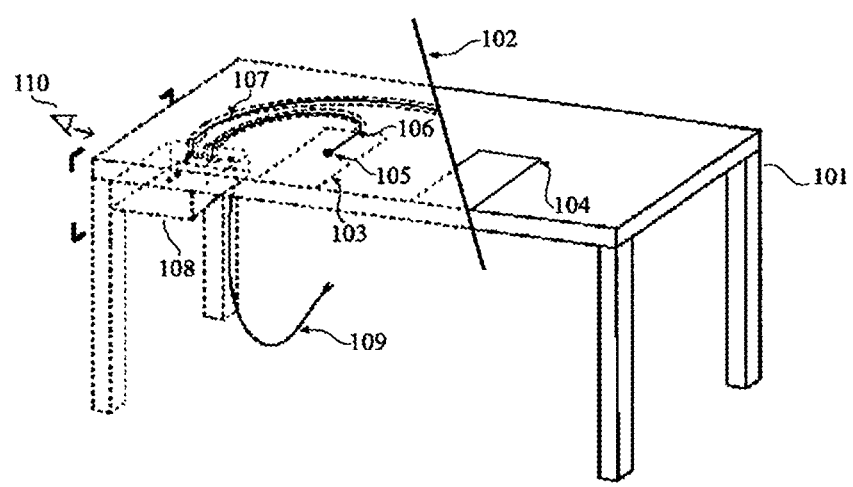
FIG. 1 provides an exemplary depiction of the ECG embedded desk.
Figure 2:
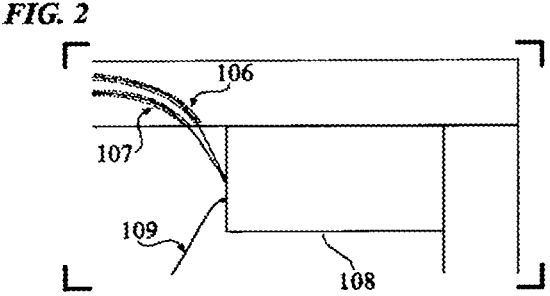
FIG. 2 provides an exemplary depiction of the side view of the computer processing device attached to the ECG embedded desk.

FIG. 1 provides an illustration of the ECG embedded desk (101). To aid in comprehension, we provide a cross-sectional view, showing both the inside (left of 102), and outside (right of 102) of the desk. Embedded in the desk (101) (and also exposed to the surface) are two electrically conductive metal sheets (left—103 and right—104) that make contact with the arms of a person using the desk (101) (left arm with left sheet—103 and right arm with right sheet—104). The sheets (103 and 104) are each connected to an interface junction (105 shows left interface, right interface not shown) that routes the measured electrical activity through wires (left wire—106, right wire—107) to a computer processing device (108). The computer processing device (108) is attached to the bottom of the desk (101), with dedicated power supplied by an electrical outlet (109). FIG. 2 provides an illustration of the computer processing device (108), and the attached wiring (left wiring—106, right wiring—107, electrical outlet—109) as seen from the left of the desk (110).

Figure 3:
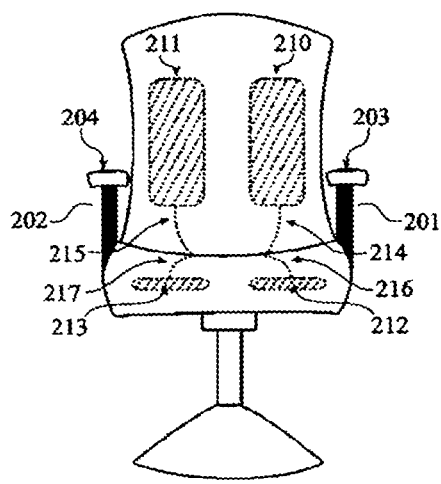
FIG. 3 provides an exemplary depiction of the front view of the ECG embedded chair.
Figure 4:
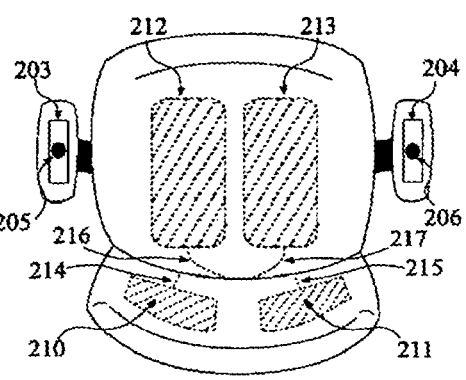
FIG. 4 provides an exemplary depiction of an aerial view of the ECG embedded chair.
Figure 5:
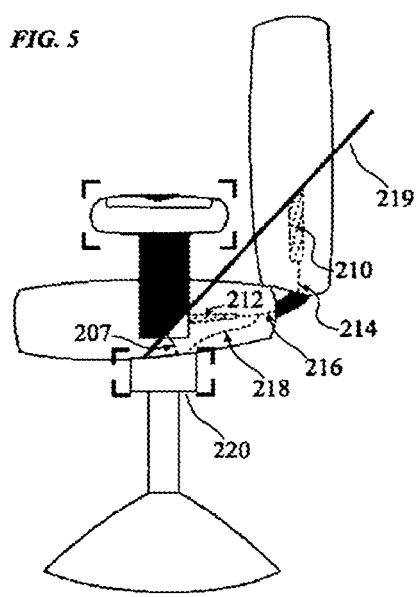
FIG. 5 provides an exemplary depiction of the side view of the ECG embedded chair.
Figure 6:
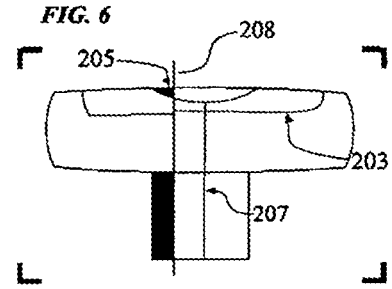
FIG. 6 provides an exemplary depiction of the cross-sectional side view of the left arm of the ECG embedded chair.
Figure 7:
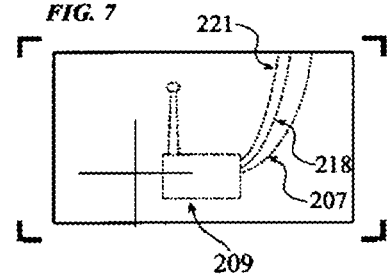
FIG. 7 provides an exemplary depiction of the Bluetooth transmission system embedded in the base of the ECG embedded chair.

FIG. 3 is the front view of the ECG embedded chair. FIG. 4 provides an aerial view, while FIG. 5 represents the left side view. FIG. 6 provides a cross-sectional view of the left arm (201), showing it from the inside (right of 208) and outside (left of 208). FIG. 7 represents the Bluetooth transmission system (220), embedded in the base of the chair, that sends signal measurements from the chair to the computer processing device (FIG. 1—108) affixed under the desk (FIG. 1—101). These drawings are described in greater detail below.

Within the arms of the chair (left arm—201 and right arm—202), there are two electrically conductive metal sheets (left—203 and right—204) situated such that a user's arms would make contact with the two sheets (left arm with left sheet—203 and right arm with right sheet—204) while seated on the chair. The signal measured by the electrically conductive metal sheets are transmitted by way of an interface junction (left interface junction—205 and right interface junction—206), connecting wires embedded in the arms of the chair (left wire—207, right wire shown in FIG. 7—221) to a Bluetooth transmitter (209) that routes the collected signals to the computer processing device (FIG. 1—108) affixed under the desk (FIG. 1—101).

The ECG embedded chair contains embedded pressure sensor panels on the seat back (left—210, right—211) as well as the seat cushion (left—212, right—213); the pressure panels detect a user's presence. From each pressure sensor panel are wires (left seat back—214, right seat back—215, left seat cushion—216, right seat cushion—217) that, as seen in FIG. 5, join together (218) within the seat cushion; the wiring (218) connects the pressure sensors to the Bluetooth transmitter (209) as seen in FIG. 7.

To aid in comprehension, FIG. 5 includes a cross-sectional view showing the inside (right of 219) as well as the outside (left of 219) of the left side view of the chair. The Bluetooth transmission system (220) is embedded within the base of the chair, it transmits the ECG and/or the pressure signal to the desk's computer processing device (FIG. 1—108).

Figure 8:
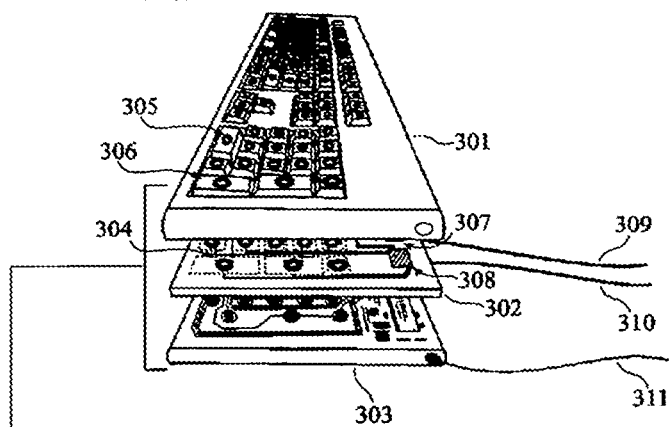
FIG. 8 provides an exemplary depiction of the ECG embedded computer keyboard.

FIG. 8 illustrates an ECG-embedded keyboard. FIG. 8 provides a right-side view of the keyboard taken apart to visualize the three main layers (from the top: keys 301), ECG transmission board (302, key-logging circuit board with casing 303). Within the ECG transmission board (302) are cylindrical interface junctions (304); at the time of a key-press, an electrically conductive cylinder (305) embedded in each key makes contact with these interface junctions (304). The electrically conductive cylinders extrude past the surface of the keys, making contact with the user's fingers, as they use the device. Signals are transmitted from the user, through the electrically conductive cylinders (305) via the cylindrical interface junctions (304), routed through a printed circuit board to a circuit junction (left side circuit junction—(307, right side circuit junction—308). Each circuit junction terminates in a wire respectively (left wiring—309, right wiring—310) from the ECG board (302); the wiring connects the ECG board to the desks computer processing device (FIG. 1—108), with a dedicated cable (311) for the transmission of key-stroke information.

Figure 9:
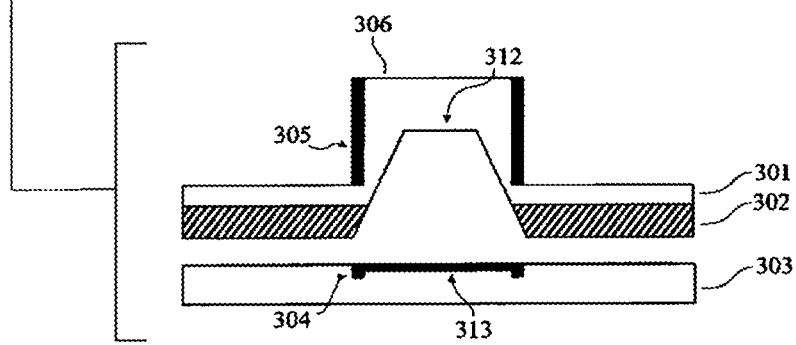
FIG. 9 provides an exemplary depiction of the cross-sectional view of a key within the ECG embedded computer keyboard.

To aid in comprehension, FIG. 9 provides a closer view of a single key (306), and its interior. The thick lines represent an electrically conductive cylinder (305) and its respective cylindrical interface junction (304). During a user's keystroke, a flexible plastic protrusion (312) stemming from a plastic overlay is compressed, and flips down to make contact with the key-stroke logging interface (313) for the transmission of key-stroke information; furthermore, during a user's key-stroke, the electrically conductive cylinder (305) makes contact with the cylindrical interface junction (304), allowing for the transmission of electrophysiological information.

Figure 10:
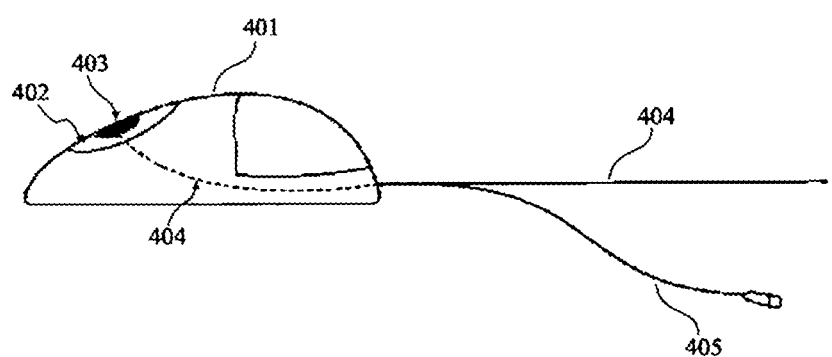
FIG. 10 provides an exemplary depiction of the ECG embedded computer mouse.

FIG. 10 provides a side view of an ECG-embedded mouse (401). The palm rest of the mouse contains an exposed electrically conductive metal sheet (402) that makes contact with an individual's palm as they use the device. The sheet (402) is attached to an interface junction (403) embedded in the palm rest. The signal measured is transmitted via the interface junction (403) through a wire (404); the wiring sends signals collected from a user to the desk's computer processing device (FIG. 1—108), with a dedicated power supply from an electrical outlet (405).

Figure 11:
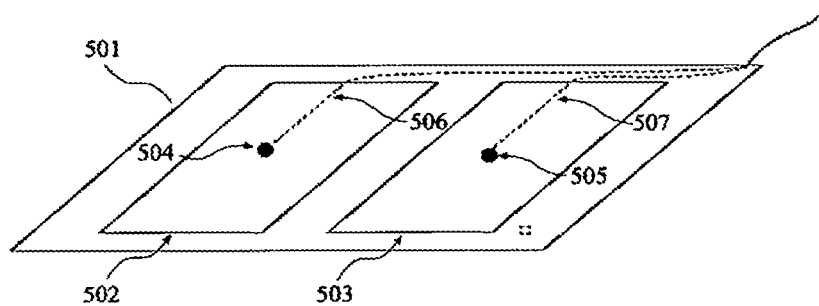
FIG. 11 provides an exemplary depiction of the ECG embedded floor mat.
Figure 12:
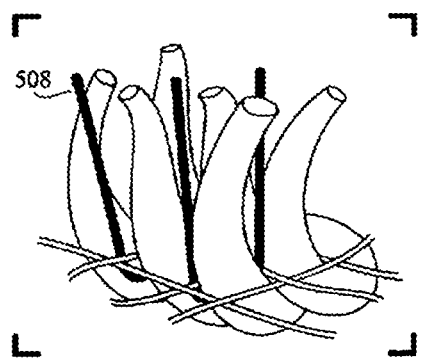
FIG. 12 provides an exemplary depiction of a closer view of the fibers within the ECG embedded floor mat.

FIG. 11 provides an illustration of an ECG-embedded mat (501), while FIG. 12 illustrates a closer view of the fibers that make up the mat. Within the mat (501) are embedded multiple electrically conductive metal fibers (508) distributed across two areas of the mat (left —502, right—503) such that a user's feet would make contact with them (left foot with left area —502, right foot with right area—503). The areas are each connected to an interface junction (left interface junction—504, right interface junction—505) that routes the measured electrical activity through electrical wires (left wire—506, right wire—507) to the computer processing device (FIG. 1—108).

Figure 13:
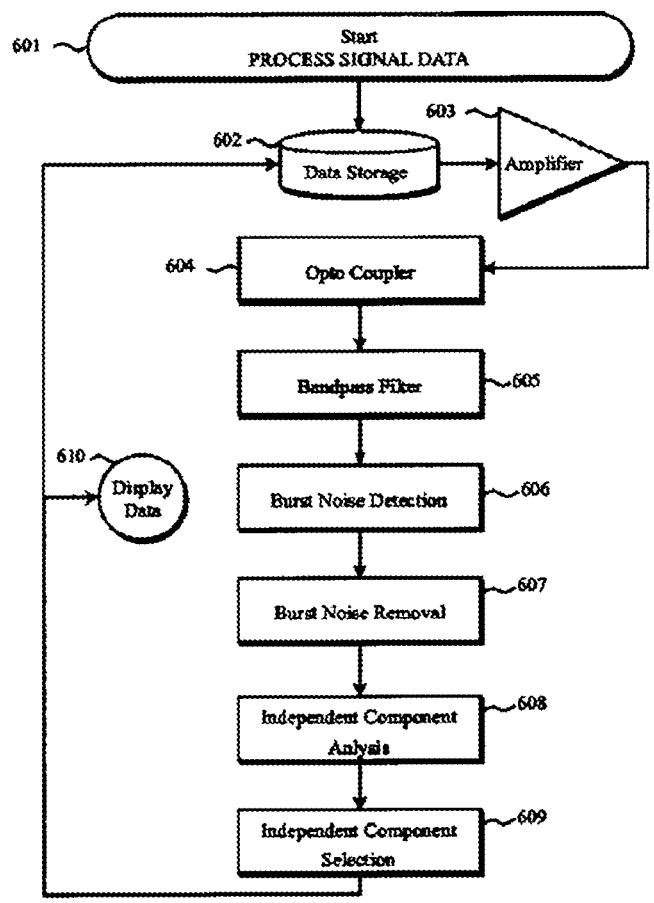
FIG. 13 is an exemplary depiction explaining the signal refinement methodology.

FIG. 13 illustrates the algorithm used by the computer processing device (FIG. 1—108) to collect, process, and store the electrophysiological data collected from a user. To begin (601), the algorithm routes a digitally sampled version of the analog signal to a storage location (602). The digital version of the signal is then routed to an ECG amplifier (603), followed by an optocoupler (604). A band-pass filter is applied (605) to remove noise from the signal. Next, irregularities are detected (606) and removed (607). Finally, independent component analysis is applied to the cleansed signal (608), and the subset of the independent components that best represent the ECG are retained (609). Finally, the data is displayed to the user, and stored for later use (602).

Figure 14:
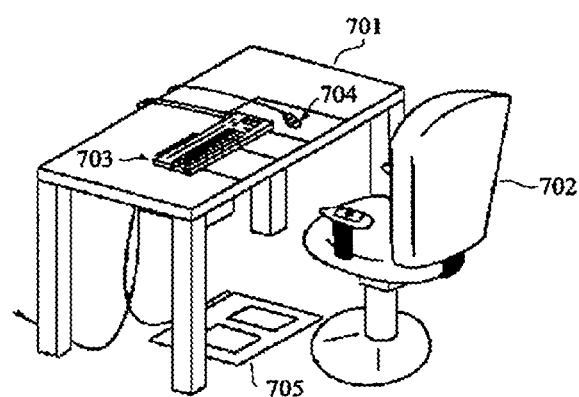
FIG. 14 provides an overview of the invention.

FIG. 14 illustrates the overview of the invention. FIG. 14 entails, an illustration of an ECG-embedded desk (701), an illustration of an ECG-embedded chair (702), an illustration of an ECG-embedded keyboard (703), an illustration of an ECG-embedded mouse (704), and an illustration of an ECG-embedded mat (705).

What is claimed:

1. A system for the measurement of heart electrical activity, the system comprising:
   a desk having:
      a. one or more electrically conductive sheets embedded in a top surface of the desk and exposed at the top surface;
      b. one or more interface junctions and a first system of wires that routes electrical activity measured at the one or more conductive sheets to a computer processing device;
      c. an electrical outlet,
   a plurality of secondary sensing devices external to the desk, each having a corresponding secondary system of wires that routes electrical activity to the computer processing device,
   wherein a set of sensing devices comprises the desk and the plurality of secondary sensing devices;
   wherein the computer processing device comprises:
      a. an amplifier;
      b. a central processing unit;
      c. random access memory;
      d. disk storage;
      e. a wireless receiver;
      f. an optocoupler,
   wherein the computer processing device;
   identifies a first subset of the set of sensing devices from which a first plurality of discrete signal components each representing and ECG measurement are retrieved during a first time period;
   retrieves the first plurality of discrete signal components;
   analyzes the first plurality of discrete signal components retrieved from the first subset to determine which of the first plurality of discrete signal components best represents an ECG of a user,
   identifies a second subset of the set of sensing devices from which a second plurality of discrete signal components each representing an ECG measurement are retrieved during a second time period,
   retrieves the second plurality of discrete signal components;
   analyzes the second plurality of discrete signal components retrieved from the second subset to determine which of the second plurality of discrete signal components best represents an ECG of the user; and
   outputs ECG data based on the signal components of each of the first plurality and the second plurality of discrete signal components determined to best represent the ECG of the user,
   wherein the first plurality of discrete signal components each correspond to the first time period such that the signal components are generated simultaneously.

2. The system of claim 1, wherein at least one of the plurality of secondary sensing devices external to the desk is a keyboard for the measurement of heart electrical activity, the keyboard comprising:
   one or more keyboard keys;
   an ECG transmission board;
   a key-logging circuit board;
   one or more electrically conductive cylinders embedded in each key;
   one or more cylindrical interface junctions that routes electrical activity through a printed circuit board,
   wherein the printed circuit board is in communication with the computer processing device by way of the second system of wires.

3. The system of claim 2, wherein a second of the plurality of secondary sensing devices external to the desk is one of a chair, a mouse, and a mat.

* * * * *